United States Patent

Gautschi et al.

Patent Number: 6,123,974
Date of Patent: Sep. 26, 2000

[54] HYDROXY-METHYL-HEXANONES AS FLAVORING AGENTS

[75] Inventors: Markus Gautschi, Zeiningen; Luis Ibañez, Dübendorf, both of Switzerland

[73] Assignee: Givaudan Roure (International) SA, Geneva, Switzerland

[21] Appl. No.: 09/295,169

[22] Filed: Apr. 20, 1999

[30] Foreign Application Priority Data

Apr. 20, 1998 [EP] European Pat. Off. ............... 98810338

[51] Int. Cl.[7] ........................... C07C 49/17; C07C 45/42; A23L 1/226
[52] U.S. Cl. ........................... 426/534; 426/590; 426/598; 426/629; 426/634
[58] Field of Search .................................... 426/534, 533, 426/590, 598, 629, 634

[56] References Cited

FOREIGN PATENT DOCUMENTS

| 0 482 834 A1 | 4/1992 | European Pat. Off. |
| 63-5050 | 1/1988 | Japan. |
| 3-167150 | 7/1991 | Japan. |
| 4-120043 | 4/1992 | Japan. |

OTHER PUBLICATIONS

Moio, et al., *Ital. J. Food Sci.*, vol. 4, No. 4, pp. 441–447 (1994).
Derwent English language abstract of JP 4–120043 (B2).
Derwent English language abstract of JP 3–167150 (B3).
Derwent English language abstract of JP 63–5050 (B4).
Excerpt from database (Volatile Compounds in Food, VCF--base.)

*Primary Examiner*—Anthony J. Weier
*Assistant Examiner*—Robert Madsen
*Attorney, Agent, or Firm*—Mark E. Waddell; Stephen M. Haracz; Bryan Cave LLP

[57] ABSTRACT

The present invention relates to new α-hydroxyketone compositions. In particular, there is provided 3-hydroxy-5-methyl-hexan-2-one, 2-hydroxy-5-methyl-hexan-3-one and mixtures thereof. These compounds have utility as flavoring and masking agents for, e.g., food and beverages. Processes for making such compounds also are provided.

12 Claims, No Drawings

HYDROXY-METHYL-HEXANONES AS FLAVORING AGENTS

FIELD OF INVENTION

The present invention relates to hydroxy-methyl-hexanones, namely 2-hydroxy-5-methyl-hexan-3-one and mixtures of this compound, with 3-hydroxy-5-methyl-hexan-2-one. The present invention also relates to flavoring and/or masking compositions, food or beverages flavored with the above compounds, and a process for preparing these compounds.

BACKGROUND OF THE INVENTION

The skilled person in the food and beverage industry knows of the critical role flavor plays in the appreciation of food and beverages. Many food products, such as cocoa, chocolate, coffee, caramel, nuts, malt and the like have flavor quality that is referred to in the language of this art as "roasted brown." For purposes of the present invention, the term "roasted brown" will be used to describe flavor properties of the mentioned food products, as well as of food products having similar flavor characteristics. As used herein, the term "flavor" is intended to mean flavor, aroma and/or taste.

From the above group of food products, flavor is especially important for chocolate. Fine flavor, high nutritional value, pleasing appearance and good storage qualities make chocolate a food product of exceptional value which is very popular and widely used. The flavor of chocolate depends on the quality and origin of the cocoa beans, on the processing thereof and the preparation of the chocolate. The processing steps which influence the chocolate quality include fermentation, drying, roasting, cleaning and milling of the cocoa beans. In the preparation of chocolate, the ratio of cocoa mass, sugar and cocoa butter, etc. determines the flavor of the product. The flavor of chocolate has been thoroughly investigated and many volatiles contributing to the overall flavor have been determined (I. Flament, "Coffee, cacao and tea in Volatile compounds in foods and beverages," H. Maarse, Ed., Marcel Dekker, Inc. New York, 1991; Grosch, Lehrbuch der Lebensmittelchemie, 4. Ed. 1997). Compounds mainly contributing to the cocoa flavor are aldehydes, especially isovaleraldehyde and phenylethanal, as well as the corresponding aldol condensation product 5-methyl-2-phenyl-2-hexenal.

Many chocolate and cocoa based foods and beverages produced by the food industry lack flavor characteristics of high quality chocolate and cocoa. A great deal of effort has been expended to provide compounds with a natural chocolate or cocoa flavor for imparting the flavor of high quality chocolate and cocoa to products of low quality. U.S. Pat. No. 3,582,360 reportedly discloses unsaturated aldehydes, especially 2-phenyl-2-alkenals, for preparing flavor compositions and food products, particularly with chocolate and cocoa flavor.

Also, other food products with roasted brown flavor lack this freshly processed flavor. This short coming substantially reduces the overall organoleptic impression of the freshly roasted product. The missing flavor note is described as green, pungent and cocoa-like. The deficiency in roasted brown flavor is mainly due to a decrease of isovaleraldehyde. Isovaleraldehyde is relatively highly volatile, has a high reactivity towards alcohols, such as propylene glycol used as solvent in the flavorings, and undergoes aldol reactions with other aldehydes, such as phenylethanal, present in the flavorings.

The α-hydroxyketones are another example of a flavorant. α-Hydroxyketones are reportedly well represented in food products. One example is acetoin (3-hydroxy-2-butanone) which has a buttery, creamy character and which can be found in a great number of food products (Volatile compounds in food, qualitative and quantitative data, TNO Nutrition and Food Research, supplement 5, H. Maarse, C. A. Visscher, L. C. Willemsens, L. M. Nijssen, M. H. Boelens, Eds., 1994). The compound 3-hydroxy-5-methyl-2-hexanone was reportedly found in water buffalo milk and its odor (GC sniffing) was described as similar to melted cheese (L. Moio, E. Semon, J. L. Le Quere, *Ital. J. Food Sci.* (1994), 4, 441).

The literature reportedly describes different methods for producing α-hydroxyketones. For example, JP-A2-04120043 reportedly discloses the synthesis of α-hydroxyketones by oxidizing olefins with $H_2O_2$ under acidic conditions. EP-A1-0 482 834 reports the preparation of α-hydroxyketones by oxidizing olefins with peracetic acids in the presence of an Ru catalyst. JP-A2-03167150 reportedly describes the synthesis of α-hydroxyketones by oxidation of alkynes with oxygen in the presence of silanes and a Co catalyst. JP-86-150522 reportedly describes hydrolysis of α-halo arylketones in the presence of alkali-hydroxides to prepare α-hydroxarylketones.

From the discussion above, it is clear that there is a need for compounds which can be incorporated into, e.g., food and beverage products to impart roasted brown flavor thereto.

Accordingly, one object of the present invention is to provide compounds which are useful in imparting roasted brown flavor to food and beverage products.

Another object of the invention is a process for producing novel α-hydroxyketones.

These and other objects of the invention will become apparent from the disclosure and claims set forth herein.

SUMMARY OF THE INVENTION

The present invention provides novel α-hydroxyketone compound including 2-hydroxy-5-methyl-hexan-3-one, 3-hydroxy-5-methyl-hexan-2-one and mixtures thereof.

Another embodiment is a soybean-based food or beverage containing a mixture of 3-hydroxy-5-methyl-hexan-2-one and 2-hydroxy-5-methyl-hexan-3-one.

Another embodiment is a process for preparing an α-hydroxyketone. This process includes reacting 5-methyl-2-hexanone with sulfuryl chloride to produce 3-chloro-5-methyl-2-hexanone; forming 3-acetoxy ketone from 3-chloro-5-methyl-2-hexanone; and hydrolyzing the 3-acetoxyketone to form one or more α-hydroxyketones.

DETAILED DESCRIPTION OF THE INVENTION

It has now been found that roasted brown flavor can be imparted to, e.g., food and beverage products by including the novel compound of formula (I) set forth below:

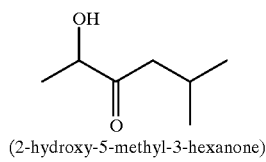

(2-hydroxy-5-methyl-3-hexanone)

In another embodiment of the present invention, it has been found that a novel mixture of the compound of formula (I) with a compound of formula (II):

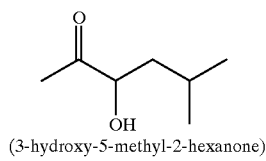

(3-hydroxy-5-methyl-2-hexanone)

imparts a similar sensory flavor impression of isovaleraldehyde to roasted brown flavorings, food products and beverages.

These new compounds and mixtures are especially useful for enhancing the flavor of flavoring compositions and food and beverage products with roasted brown flavoring characteristics.

As used herein, 2-hydroxy-5-methyl-3-hexanone is used interchangeably with 2-hydroxy-5-methyl-hexan-3-one. Similarly, 3-hydroxy-5-methyl-2-hexanone is used interchangeably with 3-hydroxy-5-methylhexan-2-one.

It also has been found that the two hydroxyketones (formulas (I) and (II)) of the present invention have a green, pungent, roasted and cocoa-like flavor. Mixtures of these hydroxyketones impart the pungent, cocoa-like note of isovaleraldehyde to chocolate, cocoa and other products with roasted brown flavor. Therefore, the hydroxyketones of the present invention are useful for enhancing or modifying the flavor profile of roasted brown flavors like cocoa, chocolate, coffee, caramel, toffee, roasted and regular nuts, such as, for example, hazelnuts, almonds, walnuts, chestnuts, macadamia, coconut, roasted butter, condensed milk, malt and the like. The compounds of the invention are especially useful to enhance the powdery and cocoa-like notes of cocoa and other roasted brown flavor notes.

Flavoring compositions with the roasted brown flavor profile enhanced or modified with the hydroxyketones of the present invention are useful to impart freshly processed brown flavor qualities to food and beverage dairy products, such as, for example, UHT milk, condensed milk, yogurt, cream desserts, cheese, bakery products such as bread, biscuits, cookies, cakes, crackers, cereals and confectionery products, such as, for example, chocolate assortments, caramels, toffees and butterscotch.

Further, it has been found that the hydroxyketones of the present invention also act as masking agents in soybean derived products; while at the same time enhancing the flavor quality of these products. Soybean products like soybean milk, soybean yogurt, tofu, etc. have a cereal and nut-like character, i.e. such foods are accompanied by a typical green vegetable note.

Many consumers consider the green vegetable note as a drawback. Therefore, a masking agent for this typical green vegetable note in soybean products is of great value for the industry. The undesirable green vegetable and beany off-flavor of soy protein has been reduced by treatment with porcine liver aldehyde oxidase (P. Maheshwari, P. A. Murphy, Z. L. Nikolov, *J. Agric. Food Chem.* 1997, 45, 2488), by treatment with liquid and supercritical carbon dioxide (P. Maheshwari, E. T. Ooi, Z. L. Nikolov, *J. Am. Oil Chem. Soc.* 1995, 72, 1107) and by fermentation with *Bacillus subtilis* and *Bacillus natto* (S. H. Choi, Y. A. Ji, *Korean J. Food Sci. Technol.* 1989, 21, 229).

Surprisingly, by the addition of the hydroxyketones of the present invention, not only are the undesirable green vegetable and beany notes of soybean products remarkably reduced, but at the same time, the cereal nutty characteristics are enhanced. This results in a product with a more overall accepted flavor profile that is no longer associated with the negative green vegetable flavor of soybean derived products.

The compounds of the present invention are also useful when combined in food and beverages having other flavor characteristics, such as fruit products, diary products, vegetable products, meat products, spices, herbs, pharmaceutical products, oral hygiene products and the like.

The hydroxyketones of the present invention, for example, can be incorporated into a product, such as a flavor composition including the usual additives known to those skilled in the art. When the hydroxyketones of the present invention are used in flavoring compositions to enhance, modify or mask existing flavors or to provide a characteristic impression, they may be incorporated into the flavoring compositions alone or in combination with additional flavor ingredients used for food products.

Additional flavoring ingredients which create roasted brown flavorings to be added to the above-referenced flavor composition include esters, aldehydes, ketones, alcohols, lactones, heterocycles, such as, for example, furans, pyridines, pyrazines and sulfur compounds, such as, for example, thiols, sulfides, disulfides, and the like. These components can be combined in proportions normally used in the art for the preparation of such flavoring compositions.

When the hydroxyketones of the present invention are used in flavoring compositions having a roasted brown flavor profile, to provide or modify the characteristic impression of isovaleraldehyde, especially as in cocoa and chocolate flavoring compositions, they may be combined with isovaleraldehyde. Isovaleraldehyde, usually present in chocolate, cocoa and other flavorings, can be partially or completely substituted by the hydroxyketones of the invention. The combination of the compounds of the present invention with isovaleraldehyde is preferred for cocoa and chocolate-flavoring compositions because of their milk chocolate-like flavor.

The amount of hydroxyketone(s) of the present invention used in the various compositions described herein depends on the precise organoleptic character desired in the finished product. For example, in the case of flavoring compositions, the amount of hydroxyketone(s) of the present invention incorporated therein will vary according to the food or beverage in which the flavor has to be enhanced or modified. The amount of hydroxyketone(s) of the invention incorporated into the flavoring composition will also depend on whether the roasted brown flavor profile of a product has to be enhanced or modified; or whether a full rounded roasted brown flavor has to be imparted to an unflavored material.

In the later case, more of the hydroxyketone compound(s) of the invention are required. For example, a ready-to-consume product with a roasted brown flavor preferably contains at least about 1 ppm of a hydroxyketone of the present invention based on the total weight of the product. It is generally desirable not to use more than about 20 ppm in the ready-to-consume product. The desirable range of the flavoring composition in the ready to consume product corresponds to about 3 to about 6 ppm of a hydroxyketone of the present invention. The amount of the flavoring composition added to the product should not only impart the desired flavor to the product, but it should also give a balanced impression. Accordingly, a flavoring composition of the present invention preferably contains about 0.5% to about 1% of a mixture of hydroxyketones of formula (I) and (II) based on the total weight of the flavoring composition.

In the present invention, the ratio of 3-hydroxy-5-methyl-hexan-2-one to 2-hydroxy-5-methyl-hexan-3-one can vary from about 1:1 to about 99:1.

For soybean products, it is preferable to add at least about 0.1 ppm of a hydroxyketone of the present invention, based on the total weight of the product. An upper limit of 20 ppm of a hydroxyketone of the present invention based on the total weight of the product is preferred. Flavor compositions for masking the undesired soybean flavor contain preferably about 0.5% to about 1% of a hydroxyketone of the present invention based on the total weight of the flavoring composition.

It may be desirable in the flavoring compositions of the present invention to incorporate flavor delivery vehicles or carriers, such as, for example, gum arabic, maltodextrin, etc., or solvents such as ethanol, propyleneglycol, water, triacetin, etc. When the carrier is an emulsion, the flavoring composition may also contain emulsifiers such as mono- and diglycerides of fatty acids and the like. By using such carriers or solvents, the desired physical form of the flavoring composition can be obtained. The flavoring compositions of the present invention can take various forms, including, for example, spray-dried, liquid, encapsulated, emulsified or other forms.

The flavoring compositions of the present invention can be added to food and beverage by conventional methods known to the skilled person. For example, a chocolate praline may be prepared by incorporating into the flavoring composition fat, sugar, milk, cocoa powder and stabilizers and admixing of these ingredients in a conventional freezer. A powdered chocolate or cocoa mix may be prepared by admixing dried milk solids, sugar and the flavoring composition in a dry blender until uniformity is obtained. When such dry mixtures are used, the hydroxyketones or flavoring compositions of the present invention can be added to one or more of the solid ingredients or to any portion thereof. In this case, the flavoring composition may be spray-dried, encapsulated or the like.

Another embodiment of the present invention is a process for preparing the hydroxyketones of the invention in an economical way. For example, a process for making a compound according to the present invention starts from inexpensive 5-methyl-2-hexanone which is reacted with sulfuryl chloride in a first step to give 3-chloro-5-methyl-2-hexanone with high selectivity, as set forth below:

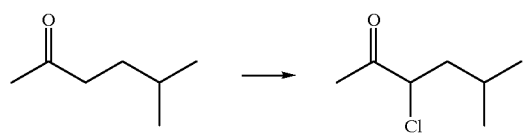

The 3-chloro-5-methyl-hexanone is treated in a second step with potassium acetate and alkali iodide:

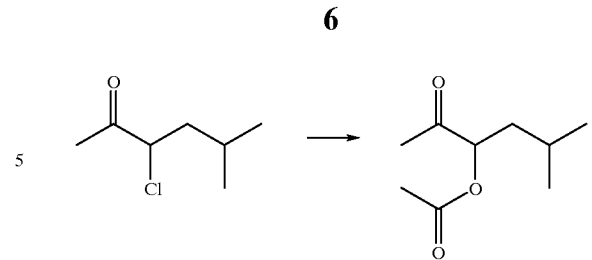

The 3-acetoxy-ketone, e.g., 3-acetoxy-5-methyl-2-hexanone obtained in the second step is hydrolyzed under alkaline conditions to give the desired 3-hydroxy-5-methyl-2-hexanone or a mixture of 3-hydroxy-5-methyl-2-hexanone and 2-hydroxy-5-methyl-3-hexanone.

The first step of the above synthesis is performed in the presence or absence of an inert solvent such as hexane, cyclohexane, benzene, toluene and the like. Hexane is preferred. The reaction is carried out between room temperature and reflux temperature, the latter being preferred.

The molar ratio of 5-methyl-2-hexanone to sulfuryl chloride may vary from about 1:1 to about 1:1.5, preferably about 1:1.2. Molar ratios of 5-methyl-2-hexanone to sulfuryl chloride below about 1.2 result in less chloroketone containing minor amounts of 3,3-dichloroketone. Molar ratios of 5-methyl-2-hexanone to sulfuryl chloride higher than 1.2 result in higher yields of chloroketone, however, formation of 3,3-dichloroketone increases. The product may be purified by distillation or directly used in the following step.

In the second step of the process according to the present invention, the 3-chloro-5-methyl-hexanone is treated with potassium acetate and an alkali iodide in an inert solvent, such as tetrahydrofuran, acetonitrile, methylvinylketone, diethylketone, acetone and the like. The reaction is preferably run in acetone at the reflux temperature. Per mol potassium acetate is 1:10 mol %, preferably 4 mol % of alkali iodide is used. Sodium iodide is preferred. The reaction mixture may be hydrolyzed with water, or preferably is filtered to remove insoluble salts and washed with water and a sodium thiosulfate solution to remove traces of iodine. The crude product is purified by distillation under reduced pressure.

The 3-acetoxy-5-methyl-2-hexanone obtained in the second step of the process is hydrolyzed in the third step with an aqueous alkaline solution to give the desired 3-hydroxy-5-methyl-2-hexanone or mixtures of 3-hydroxy-5-methyl-2-hexanone and 2-hydroxy-5-methyl-3-hexanone. The hydrolysis is carried out between 0° C. and reflux temperature depending on the desired ratio of isomeric hydroxyketones of formula (I) and (II). Preferably, the reaction is run at low temperature, i.e., closer to 0° C. than the reflux temperature, with a short reaction time using weak alkaline solution with a molar ratio of base to acetoxyketone of about 1.1 to about 1. These conditions yield 3-hydroxy-5-methyl-2-hexanone of high isomeric purity.

If the reaction is run at elevated temperature and for a long reaction time using a strong alkaline solution with a molar ratio of about 10 mol of base per mol acetoxyketone, an isomeric mixture containing approximately equal amounts of 3-hydroxy-5-methyl-2-hexanone and 2-hydroxy-5-methyl-3-hexanone is obtained. Using a weak alkaline solution and a long reaction time with a molar ratio of the base to acetoxyketone of about 1.1 to about 1 results in a mixture containing a higher amount of 3-hydroxy-5-methyl-2-hexanone.

The following examples are provided to further illustrate methods of preparation of the compounds of the present invention, as well as certain physical properties and uses thereof. These examples are illustrative only and are not intended to limit the scope of the invention in any way.

EXAMPLES

Example 1

3(2)-Hydroxy-5-methyl-hexan-2(3)-one

To a refluxing solution of 750 g (6.58 mol) 5-methyl-2-hexanone in 1.13 l n-hexane at 65° C., 1.06 kg (7.89 mol) sulfuryl chloride was added over a period of 2 h. After complete addition of the sulfuryl chloride, the reaction mixture was allowed to cool to room temperature, was washed 4 times with 150 ml $H_2O$, dried ($MgSO_4$) and concentrated in vacuo. The residue was distilled over a 5 cm Vigreux-column (80 mbar, 67–76° C.) to give 884 g of 3-chloro-5-methyl-2-hexanone in the form of a yellowish liquid (purity: 88%, impurity: 11% 3,3-dichloro-5-methyl-2-hexanone).

The chloroketone obtained was dissolved in 2 l acetone and 588 g (6 mol) potassium acetate and 37.5 g (0.25 mol) sodium iodide was added. The mixture was heated at reflux under a $N_2$-atmosphere until complete conversion was observed (about 24 h), then it was cooled to room temperature and filtered. The residue was washed with 250 ml acetone and the combined filtrates were concentrated in vacuo. The residue was taken up in 1 l MTBE (Methyl-tert-butyl ether) and filtered. The filtrate was washed with 600 ml of sodium thiosulfate solution (10%) and 3 times with 200 ml $H_2O$, dried ($MgSO_4$) and concentrated in vacuo. The crude product was distilled using a 20 cm Widmer-column (18 mbar, 92–96° C.) to give 750 g (64% yield over two steps) of 3-acetoxy-5-methyl-2-hexanone (97% purity).

To a 0° C. solution of 580 g (3.37 mol) 3-acetoxy-5-methyl-2-hexanone in 680 ml methanol, a solution of 513 g (3.7 mol) potassium carbonate in 680 ml $H_2O$ was added under vigorous stirring over a period of 1.5 h. The reaction mixture was allowed to warm overnight to room temperature. The solid potassium carbonate was removed by filtration and washed with 100 ml of MTBE. The filtrate was concentrated in vacuo and the residue was taken up in 300 ml MTBE. The organic layer was separated, washed 3 times with 150 ml brine and 1 time with 200 ml $H_2O$, dried ($MgSO_4$) and concentrated in vacuo to give 428 g (97%) crude product. Distillation using a 18 cm Widmer-column (0.06 torr, 40° C.) gave 330 g (75%) 3(2)-hydroxy-5-methyl-hexan-2(3)-one. Isomeric ratio: 78.2:21.8.

3-Hydroxy-5-methyl-hexan-2-one
NMR (400 MHz, $CDCl_3$): 0.92 (d, J=6.8 Hz, $CH_3$), 0.97 (d, J=6.8 Hz, $CH_3$), 1.18–1.22 (m, $CH_2$); 1.61 (s, $CH_3$); 2.05 (m, $CH(CH_3)_2$); 3.50 (d, J=4.8 Hz, OH); 3.87 (m, C$\underline{H}$OH). MS: 130 (0.1, M$^+$), 87 (37), 74 (17), 69 (73), 57 (13), 45 (52), 43 (100), 41 (31), 29 (5).

2-Hydroxy-5-methyl-hexan-3-one
NMR (400 MHz, $CDCl_3$): 0.80 (d, J=6.8 Hz, $CH_3$), 0.82 (d, J=6.8 Hz, $CH_3$), 1.11 (d, J=7.2 Hz, $CH_3$); 1.75 (dd, J=6.8, 16.8, 1H, $CH_2$); 1.92 (dd, J=6.8, 16.8, 1H, $CH_2$); 2.15 (m, C$\underline{H}(CH_3)_2$); 3.65 (d, J=4.8 Hz, OH); 3.89 (m, C$\underline{H}$OH). MS: 130 (0.1, M$^+$), 85 (90), 74 (13), 69 (22), 57 (100), 45 (79), 43 (39), 41 (37), 29 (14).

Example 2

A flavoring composition having a typical chocolate flavor was prepared as set forth in Table 1:

TABLE 1

| Ingredient | Parts by weight | |
|---|---|---|
| | A | B |
| Benzaldehyde | 0.02 | 0.02 |
| Cocoa extract | 85.88 | 85.38 |
| Ethyl phenyl acetate | 0.15 | 0.15 |
| Ethylvanillin | 5.00 | 5.00 |
| iso-Butyric acid | 0.05 | 0.05 |
| Phenyl acetic acid | 0.30 | 0.30 |
| Phenyl-ethyl alcohol | 0.20 | 0.20 |
| 2,3,5-Trimethylpyrazine | 0.20 | 0.20 |
| 2-Ethyl-3,5-dimethyl-pyrazine | 0.20 | 0.20 |
| Vanillin | 8.00 | 8.00 |
| 3(2)-Hydroxy-5-methyl-hexan-2(3)-one | — | 0.50 |
| Total | 100.00 | 100.00 |

The chocolate flavorings A and B were added at 0.07% to commercial pasteurized milk (3.5% fat content) sweetened with 6% sugar. The thus prepared chocolate flavored milk drinks A and B were evaluated in a blind test by an expert panel of flavorists. The panel judged the chocolate milk drink B containing a hexanone compound of the present invention to have enhanced cocoa and powdery notes, to give a more pronounced nice dark chocolate impression and to have an overall improved taste profile.

Example 3

A flavoring composition having a coconut flavor was prepared as set forth in Table 2:

TABLE 2

| Ingredient | Parts by weight | |
|---|---|---|
| | A | B |
| Ethylvanillin | 0.1 | 0.1 |
| γ-Nonalactone | 1.0 | 1.0 |
| Propylene glycol | 60.9 | 60.4 |
| Water | 38.0 | 38.0 |
| 3(2)-Hydroxy-5-methyl-hexan-2(3)-one | — | 0.5 |
| Total | 100.0 | 100.0 |

The coconut flavorings A and B were added at 0.06% to commercial pasteurized milk (3.5% fat content) sweetened with 6% sugar. The coconut flavored milk drinks A and B were evaluated in a blind test by an expert panel of flavorists. The panel judged the coconut milk drink B containing a hexanone compound according to the present invention to have a fresher coconut flesh (white part of the coconut) character and an enhanced coconut milk taste profile compared to drink A.

Example 4

A flavoring composition having a roasted hazelnut flavor was prepared as set forth in Table 3:

TABLE 3

| Ingredient | Parts by weight | |
|---|---|---|
| | A | B |
| 2-Acetyl-pyrazine | 0.2 | 0.2 |
| Benzaldehyde | 0.2 | 0.2 |

TABLE 3-continued

| Ingredient | Parts by weight | |
|---|---|---|
| | A | B |
| Diacetyl | 0.3 | 0.3 |
| Dimethyl-resorcinol | 0.2 | 0.2 |
| Methylcorylone | 0.6 | 0.6 |
| 5-Methyl-furfural | 0.4 | 0.4 |
| γ-Nonalactone | 0.1 | 0.1 |
| Propylene glycol | 95.9 | 94.9 |
| 2,3,5-Trimethylpyrazine | 0.1 | 0.1 |
| Vanillin | 2.0 | 2.0 |
| 3(2)-Hydroxy-5-methyl-hexan-2(3)-one | — | 1.0 |
| Total | 100.0 | 100.0 |

The hazelnut flavorings A and B were added at 0.05% to commercial pasteurized milk (3.5% fat content) sweetened with 6% sugar. The hazelnut flavored milk drinks A and B were evaluated in a blind test by an expert panel of flavorists. The panel judged the hazelnut milk drink B containing a hexanone compound according to the present invention to have a more rounded off roasted hazelnut flavor, a reduced harshness of pyrazine and resorcinol character and an enhanced freshly roasted and nutty character compared to drink A.

Example 5

A commercially available UHT soybean drink (Vegi Line Sojadrink, Migros MGB, CH-8031 Zürich) was flavored with 0.5 ppm 3(2)-hydroxy-5-methyl-hexan-2(3)-one (soybean drink B). An untreated (i.e., not supplemented with a hexanone according to the present invention) soybean drink (soybean drink A) and soybean drink B were evaluated in a blind test by an expert panel of flavorists. The panel judged the soybean drink B flavored with a hexanone compound according to the present invention to be much more acceptable because the undesirable green/vegetable notes typically associated with soybeans were remarkably reduced therein, giving the drink an overall pleasant flavor profile with enhanced milky/creamy and cereal/nutty notes.

Example 6

A flavoring composition having a banana flavor was prepared as set forth in Table 4:

TABLE 4

| Ingredient | Parts by weight | |
|---|---|---|
| | A | B |
| Canaga oil | 0.005 | 0.005 |
| Clove leaf oil | 0.020 | 0.020 |
| Ethyl acetate | 0.125 | 0.125 |
| Furaneol (15% in PG) | 0.133 | 0.133 |
| Isoamyl acetate | 3.470 | 3.470 |
| Isoamyl alcohol | 0.125 | 0.125 |
| Isoamyl caproate | 0.200 | 0.200 |
| Isobutyl acetate | 0.600 | 0.600 |
| Isobutyl alcohol | 0.400 | 0.400 |
| Linalool | 0.0025 | 0.0025 |
| Banana Ess. 50x | 0.100 | 0.100 |

TABLE 4-continued

| Ingredient | Parts by weight | |
|---|---|---|
| | A | B |
| Acetaldehyde | 0.025 | 0.025 |
| Propylene glycol | 94.817 | 94.717 |
| 3(2)-Hydroxy-5-methyl-hexan-2(3)-one | — | 0.100 |
| Total | 100.0 | 100.0 |

The banana flavorings A and B were added at 0.1% to water sweetened with 5% sugar. The banana flavorings A and B were evaluated in a blind test by an expert panel of flavorists. The panel judged the banana flavoring B containing a hexanone compound according to the present invention to be fuller in body and to have a truer fruit-like and riper character compared to flavoring A.

The invention being thus described, it will be obvious that the same may be varied in many ways. Such variations are not to be regarded as a departure from the spirit and scope of the invention and all such modifications are intended to be included within the scope of the following claims.

What is claimed is:

1. A 2-hydroxy-5-methyl-hexan-3-one compound.

2. A composition comprising a mixture of 3-hydroxy-5-methyl-hexan-2-one and 2-hydroxy-5-methyl-hexan-3-one.

3. A flavoring and/or masking composition comprising the composition of claim 2.

4. A flavoring and/or masking composition according to claim 3 wherein the ratio of 3-hydroxy-5-methyl-hexan-2-one to 2-hydroxy-5-methyl-hexan-3-one is from 1:1 to 99:1.

5. A flavoring and/or masking composition according to claim 4 further comprising organoleptic compounds, carriers, vehicles and mixtures thereof.

6. A food or beverage composition comprising the composition of claim 2.

7. A food or beverage according to claim 6 wherein the mixture of 3-hydroxy-5-methyl-hexan-2-one and 2-hydroxy-5-methyl-hexan-3-one is present in the food or beverage from about 0.1 ppm to about 20 ppm by weight.

8. A food or beverage according to claim 6 wherein the mixture of 3-hydroxy-5-methyl-hexan-2-one and 2-hydroxy-5-methyl-hexan-3-one is present in the food or beverage from about 3 ppm to about 6 ppm by weight.

9. A food or beverage according to claim 6 wherein the mixture of 3-hydroxy-5-methyl-hexan-2-one and 2-hydroxy-5-methyl-hexan-3-one is present in the food or beverage from about 0.5% to about 1% by weight.

10. A soybean-based food or beverage comprising a mixture of 3-hydroxy-5-methyl-hexan-2-one and 2-hydroxy-5-methyl-hexan-3-one.

11. A soybean-based food or beverage according to claim 10 wherein the mixture is present in the food or beverage in an amount of at least about 0.1 ppm by weight.

12. A soybean-based food or beverage according to claim 10 wherein the mixture is present in the food or beverage in an amount of about 0.5% to about 1% by weight.

* * * * *